United States Patent
Groke et al.

(10) Patent No.: US 9,174,068 B2
(45) Date of Patent: Nov. 3, 2015

(54) NAVIGATION DEVICE FOR BRACHYTHERAPY AND METHOD FOR OPERATING THE NAVIGATION DEVICE

(71) Applicant: SIEMENS AKTIENGESELLSCHAFT, Munich (DE)

(72) Inventors: David Groke, Nuremberg (DE); Michael Wiets, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 335 days.

(21) Appl. No.: 13/645,564

(22) Filed: Oct. 5, 2012

(65) Prior Publication Data
US 2014/0100407 A1  Apr. 10, 2014

(51) Int. Cl.
*A61N 5/00* (2006.01)
*A61N 5/10* (2006.01)
*A61B 6/12* (2006.01)
*A61B 6/00* (2006.01)

(52) U.S. Cl.
CPC ............... *A61N 5/1001* (2013.01); *A61B 6/12* (2013.01); *A61B 6/4441* (2013.01); *A61N 2005/1061* (2013.01)

(58) Field of Classification Search
CPC ............ A61N 5/01; A61N 5/103; A61N 5/1037–5/1071
USPC .............. 600/1–8, 410, 411, 424, 427
See application file for complete search history.

(56) References Cited

U.S. PATENT DOCUMENTS

| | | | |
|---|---|---|---|
| 8,346,344 B2 * | 1/2013 | Pfister et al. | 600/424 |
| 2007/0258639 A1 * | 11/2007 | Pfister et al. | 382/154 |
| 2008/0009731 A1 * | 1/2008 | Maschke | 600/439 |
| 2008/0171931 A1 * | 7/2008 | Maschke | 600/410 |
| 2008/0183071 A1 * | 7/2008 | Strommer et al. | 600/424 |
| 2009/0124896 A1 | 5/2009 | Haras | |

FOREIGN PATENT DOCUMENTS

| CN | 1724089 A | 1/2006 |
|---|---|---|
| CN | 101516266 A | 8/2009 |
| CN | 102076378 A | 5/2011 |

* cited by examiner

Primary Examiner — John Lacyk

(57) ABSTRACT

A navigation device for brachytherapy is provided. The navigation device has a 3D imaging facility which can be moved relative to an operating table, and which is designed to obtain a 3D image dataset intraoperatively for a region of the body of a patient positioned on the operating table which is to be irradiated radioactively using at least one applicator. The navigation device has a control facility which is linked to the imaging facility and is designed to generate a volume model of the region of the body, in which volume model the at least one applicator is emulated in the position indicated by the position data, from the 3D image dataset and from position data for a spatial position of the at least one applicator.

11 Claims, 4 Drawing Sheets

NAVIGATION DEVICE FOR BRACHYTHERAPY AND METHOD FOR OPERATING THE NAVIGATION DEVICE

FIELD OF INVENTION

The application relates to a navigation device for brachytherapy, by which a physician can be assisted with the radioactive irradiation of a region of a patient's body with a radioactive material. The application also relates to a method for operating the navigation device.

BACKGROUND OF INVENTION

Brachytherapy is a minimally invasive method of irradiating a tumor (e.g. a prostate carcinoma, a cervical carcinoma, a breast carcinoma or a laryngeal carcinoma) using internal radiotherapy, i.e. introducing a radioactive material into the immediate vicinity of the tumor or into the tumor in order to destroy it by radioactive irradiation. To do this, what are known as "applicators" are introduced into the body near to or directly into the tumor. Such an applicator can for example comprise a puncture needle which can for example be 20 cm long and 5 mm in diameter. Using such an applicator the radioactive material, the actual radioactive radiation source, can be introduced in the form of a "seed". The radiation sources introduced can remain in the body temporarily or for a longer time.

To be able to determine the precise position of an applicator for brachytherapy, computed tomography (CT) or magnetic resonance tomography (MRT) of the region of the body to be irradiated has until now been performed before the intervention. Using a 3D image dataset obtained in this way the precise dose distribution in the target region is calculated on an irradiation planning system. A 3D image dataset can for example indicate a property of the tissue for individual volume elements of a region of the body, such as penetrability for X-rays in the case of computed tomography. Based on the ideal dose distribution on/in the tumor the number and positions of the applicators to be introduced is then determined.

This dose planning and the acquisition of the necessary radioactive material is followed by the brachytherapy itself. To this end the patient is sedated in the sterile environment of an operating room and is put into the right position for the operation. This procedure is referred to below as positioning. The applicators are then inserted. To monitor the change in position of the applicators during the operation when they are introduced into the region of the body to be radioactively irradiated, conventional 2D fluoroscopy is performed during the operation using an X-ray unit. However, because the X-ray images to be obtained only convey a two-dimensional impression and have a relatively poor soft-tissue contrast, it is not possible to determine the precise position of the applicators in this way. Following the implantation of the applicators the patient is taken out of the sterile operating room into a computed tomography system and moved into another bed there, and the position of applicators in the region of the body is checked using computed tomography. If the applicators are not at the target position calculated using dose planning, the patient is returned to the operating room and the position of the applicators is corrected. This procedure must be repeated until the position of the applicators is correct, i.e. corresponds to the desired target position.

This repositioning may cause the applicators to be displaced, which represents a source of risk for the health of the patient, as he may suffer internal injuries. In addition, a change of location from a sterile to a non-sterile environment and back entails a large risk of infection. Time and cost are also important factors during the multiple repositioning, transportation and sterilization in whether brachytherapy can be provided cost-effectively in a hospital. Furthermore, the patient is exposed less radiation dose because of the correct position of the radiation source.

Once the position of the applicators has been successfully validated, the internal irradiation can proceed with the help of the seeds. For this the patient is taken into an irradiation room, also called the afterloading room. A check on the dose administered can generally not be measured, but it is calculated via the radiation intensity of the seed and its dwell time in the applicator. The afterloading device is likewise fed the patient's irradiation data using the dose planning system. The seed or seeds are introduced in motor-driven fashion via tubes into the applicators and remain there as long as was previously calculated in the planning. This data has until now been entered manually. The radiation source can then be moved to a different position in an applicator and remain there or else be introduced into another applicator.

In brachytherapy a very precise way of working and precise position determination play a crucial role. Otherwise the soft tissue surrounding the tumor may be damaged by the radioactive irradiation. On the other hand, it is not possible to check the position of the applicators frequently during the implantation. The risk of infection during repositioning for the recordings in the computed tomography system and the increasing X-ray dose with every examination in the operating room by an X-ray unit are undesirable.

SUMMARY OF INVENTION

An object of the present application is to enable a physician to precisely position applicators in a region of the body, without thereby exposing the patient to a high dose of X-ray radiation or a high risk of infection.

The object is achieved by a navigation device and a method according to independent claims. Developments of the application are given by the dependent claims.

The disclosed navigation device has a 3D imaging facility which moves relative to an operating table. This is designed to obtain a 3D image dataset for a region of a patient's body which is to be radioactively irradiated by at least one applicator. The relative mobility between navigation device and operating table makes it possible to obtain the 3D image dataset intraoperatively, i.e. while the patient is positioned on the operating table. The relative mobility of imaging facility and operating table can be achieved in that the operating table is fixed to the floor and the imaging facility is movably mounted or else conversely a permanently mounted imaging facility and a movable operating table are provided. Mixes forms of these two methods of operation are also possible. A suitable imaging facility can for example be realized by an angiography system or an X-ray C-arm system, e.g., with the support of DynaCT product from the company Siemens AG.

Another important element of the disclosed navigation device is a control facility which is linked to the imaging facility. The control facility can for example be a program or dedicated hardware of a computer, which is linked to the imaging facility for exchanging data for example via a data network.

The control facility is designed to generate a volume model of the region of the body. The control facility here forms the volume model from the 3D image dataset and on the basis of position data, e.g. coordinates and direction vectors, for a spatial position of the at least one applicator. The volume model makes the region of the body with the at least one applicator is thus emulated, which applicator is here located in the position indicated by the position data. It is not necessary here for the at least one applicator to also actually be located in the region of the body during this. The volume model can be calculated before the at least one applicator is introduced. The position data can for example be target value data for a target position which the least one applicator is to take up in the region of the body for the radioactive irradiation. This target value data can originate e.g. from the dose planning described in the introduction. The shape of the at least one applicator can be described by model data.

In just the same way provision can however also be made for an actual, instantaneous position of the at least one applicator in the region of the body to be emulated by the volume model. For this too the at least one applicator need not be mapped by the 3D image dataset. Instead the model data describing the shape is again taken as the basis.

The disclosed navigation device has the feature that the 3D image dataset can be obtained using the imaging facility while the patient is already lying on the operating table and is being prepared for the operation. As a result the organs in the region of the body which is to be irradiated have already assumed the position which they will also have during the implantation of the applicator. The patient does not need to be repositioned, potentially changing the position of the organs or the applicators in the process. This current position of the organs is then also reflected by the volume model.

In that the control facility can here combine any position data of an applicator with the 3D image data of the region of the body to form a volume model, the navigation device can be used differently for brachytherapy. However, the complete procedure can always be performed in a sterile operating environment (intraoperatively). Conventionally this is only possible if the applicators are introduced under 2D X-ray control.

The problem with this is that the orientation of an X-ray device plays a crucial part in the decision as to whether a physician can thereby also correctly identify the position of an introduced applicator. Because of foreshortening in the mapping of the applicator or mutual shadowing of applicators or shadowing of an applicator by, e.g. a bone, it can happen that the position cannot be identified and an X-ray recording is hence useless and the recording must be repeated.

The disclosed navigation device can here be developed for the use of a projection unit for generating 2D projection data of the region of the body, in other words also of a conventional X-ray device, in order to prevent such unsuitable projections. A projection unit is provided for this purpose, and is designed to be mobile relative to the operating table. For example, an X-ray C-arm can be provided as a projection unit. The control facility is then designed to establish the orientation of the projection unit in respect of the operating table on the basis of the volume model. On the basis of the volume model the control facility can here be used to identify which orientation the projection unit must have in order to produce a mapping, i.e. suitable 2D projection data, suitable for the navigation of the applicator. Specially adapted organ programs for a corresponding X-ray device can also be made available for displaying an optimal soft-tissue contrast.

The term "orientation of the projection unit" means e.g. the position of the projection unit and/or its orientation in the x, y, z direction, LAO (Left Anterior Obligue), RAO (Right Anterior Obligue), cranial, caudal. The orientation is selected such that it satisfies a predetermined optimization criterion. A foreshortening of the mapping of the at least one applicator becomes minimal or at least less than a predefined value. If several applicators are present, an additional or alternative optimization criterion can be predefined whereby a superimposition of mappings of the applicators is minimal or less than a predetermined value.

The volume model can here be formed both for a simulated position of the applicators on the basis of the target position data or however also on the basis of position data which indicates the actual, instantaneous position of the applicator or applicators.

To record the current position of the at least one applicator, a development of the navigation device provides a location facility for recording the current position and for generating corresponding current position data. Such a location facility can for example be implemented in that markers are attached to the at least one applicator and can be detected electromagnetically with the aid of trilateration or else by image recognition, e.g. by a camera or in X-ray images. Use can here be made of location systems known per se from the prior art for surgical instruments. The location facility provides the additional feature that the navigation device can generate a volume model in which the position of the at least one applicator can be checked at any desired time during the implantation.

This can firstly be used to track the orientation of the previously described projection facility, in other words e.g. the X-ray unit. Another embodiment of the navigation device in contrast provides a display facility which is set up to generate and display a representation of the region of the body obtained from the volume model and of the at least one applicator located therein. A sectional view of the volume or else a wafer representation or an artificial X-ray image can for example be generated as a representation. This visualization can be adapted at regular intervals to a changing position of the at least one applicator, so that a live representation of the navigation is produced, i.e. a permanently updated representation.

Another feature arises here, if a verification facility is also provided which is set up to determine a dose distribution of the radioactive irradiation likely to arise in the region of the body during the radioactive irradiation on the basis of the volume model. The dose distribution arising as a function of the position of the at least one applicator can for example be displayed in the live representation during the navigation. Thus it is possible for a physician to bring the boundaries of the radioactively irradiated partial volume very precisely into congruence with the boundaries of the tumor. The verification facility can also be used to check, after the implantation, whether the desired dose distribution is present in a tumor. The verification facility can for example be a simulation program for calculating the radiation distribution.

As already explained, the navigation device can be used to generate the volume also on the basis of target value data for a target position. The target value data can here likewise be determined by a dose planning facility, which makes it possible for example on the basis of a 3D image dataset obtained preoperatively using a computed tomography system or a magnetic resonance tomography system, as well as a simulation of a dose distribution, to determine a target position of the applicators suitable for the irradiation.

In connection with the dose planning facility a development of the navigation device further provides for a quantity of the radioactive material needed for the irradiation to be additionally determined by the dose planning facility and for the determined quantity automatically to generate order data for an order system, after the desired target position and the desired dose distribution have been determined. The dose planning facility is to this end set up so that a rule can be predefined, which as a function of a determined quantity of the radioactive material generates order data which can be interpreted by the order system used in the respective hospital. Because the rule can be predefined, for example a template on the basis of XML data (XML—Extensible Markup Language), the order process can be adapted to the existing order system. This enables automated procurement of the material. This gives the feature that after establishing the target position and the dose distribution a physician has no administrative effort to procure the material.

A preoperatively obtained 3D image dataset can also be used to reduce the amount of radiation the patient is exposed to when image data is obtained during the operation. To this end a development of the navigation device provides that its control facility is designed to combine, i.e. merge, the intraoperatively obtained 3D image dataset with the preoperatively obtained 3D image dataset to form a combined 3D image dataset, and to generate the volume model from the combined 3D image dataset. The intraoperatively obtained 3D image dataset can thus be obtained using a low radiation dose, as for example is possible with the X-rays and DynaCT product from the company Siemens AG, which to this end has a "Low Dose" mode. The combination or merger of the image datasets can be performed on the basis of anatomical circumstances and distinctive shapes of the organs (landmarks) using algorithms known per se, which merge the intraoperatively obtained 3D image dataset with the preoperatively obtained 3D image dataset. A further feature of using a preoperatively obtained 3D image dataset is that computed tomography systems and/or magnetic resonance tomography systems can be used for this, permitting a higher-contrast resolution of the soft tissue of the body than an imaging facility that can be operated in an operating room.

The disclosed navigation device is possible to execute the following method steps which make up the disclosed method.

The imaging facility, in other words possibly the DynaCT, enables 3D image data is recorded for a patient positioned on the operating table. The control facility, in other words possibly a personal computer, enables position data on the position of the at least one applicator is received, wherein this can relate to a target position determined by a dose planning facility or else an actual position captured by a location facility. The control facility enables the described volume model is then also generated and on the basis of the volume model the position of the at least one applicator in the region of the body is visualized. This can happen in two ways, namely either a) by controlling a projection unit, in other words e.g. an X-ray unit, to establish the latter's orientation in respect of the patient couch and subsequent generation of 2D projection data by the projection unit or b) by direct generation of a representation of the region of the body and of the at least one applicator on the basis of the volume model itself.

Also belonging to the application are developments of the disclosed method, which have features which correspond to the features of the developments of the disclosed navigation device. To avoid repetitions the features of said developments of the method are not described again here.

BRIEF DESCRIPTION OF THE DRAWINGS

In the following the application is explained once again in greater detail on the basis of an embodiment.

DETAILED DESCRIPTION OF INVENTION

In the example explained below the components of the navigation device described and the steps of the method described each represent individual features of the application to be considered separately from one another, and which also develop the application independently of one another and thus are also to be regarded individually or in a combination other than the one shown as a component of the application. Furthermore, the embodiments described can also be supplemented by others of the features of the application already described.

Figure 1:
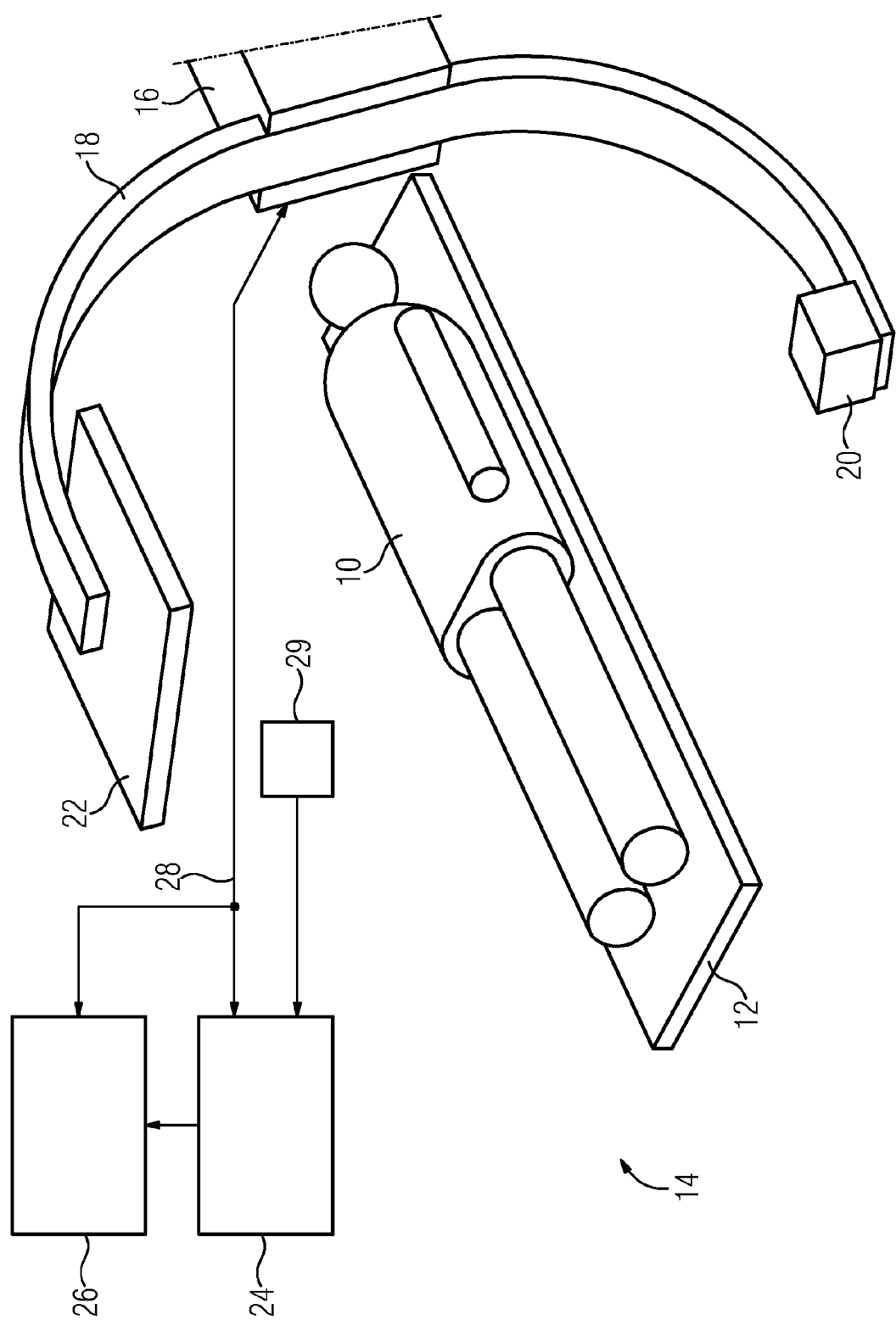
FIG. 1 shows a schematic representation of an embodiment of the disclosed navigation device, as it may be set up in an operating room.

FIG. 1 shows a patient 10 who is positioned on an operating table 12. The patient 10 is prepared for an operation in the context of brachytherapy and if possible should not change his position during the implantation of applicators for the brachytherapy. In order to monitor the position of the applicators during implantation, a navigation device 14 is provided in the operating room in which the operating table 12 is located. The navigation device 14 comprises an imaging facility 16 which is positioned so as to move in respect of the operating table 12; in the example in FIG. 1 this can be an X-ray C-arm 18 or a MRT device which can rotate about the operating table 12. The imaging facility 16 can in the first case for example comprise an X-ray source 20 and an X-ray flat-panel detector 22, so that it can also be used during the operation as a projection unit for obtaining two-dimensional X-ray images. The imaging unit 16 can be the X-ray and DynaCT product from Siemens AG, two X-ray sources and two detectors being used in order to reduce the recording time for the provision of an individual 3D image dataset and to enable the sight out of the two different angulations The imaging unit 16 is linked to a control unit 24 and a display unit 26. The control facility 24 can for example comprise a personal computer or a workstation computer. The display unit 26 can for example be a monitor or another personal computer with a monitor. The link can for example be effected by a data network 28, such as an Ethernet.

Figure 2:
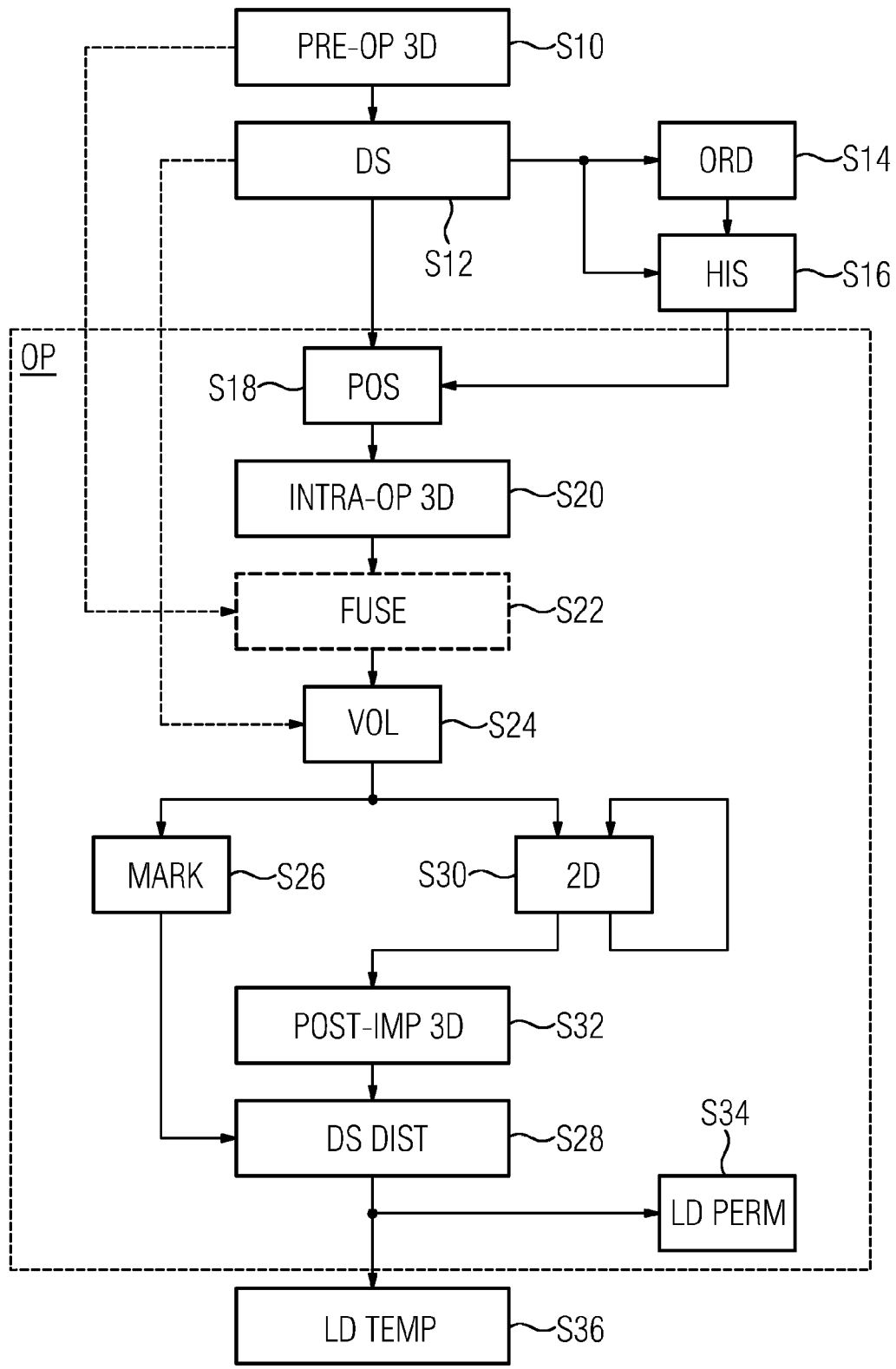
FIG. 2 shows a flow chart to clarify different embodiments of the disclosed method.
Figure 3:
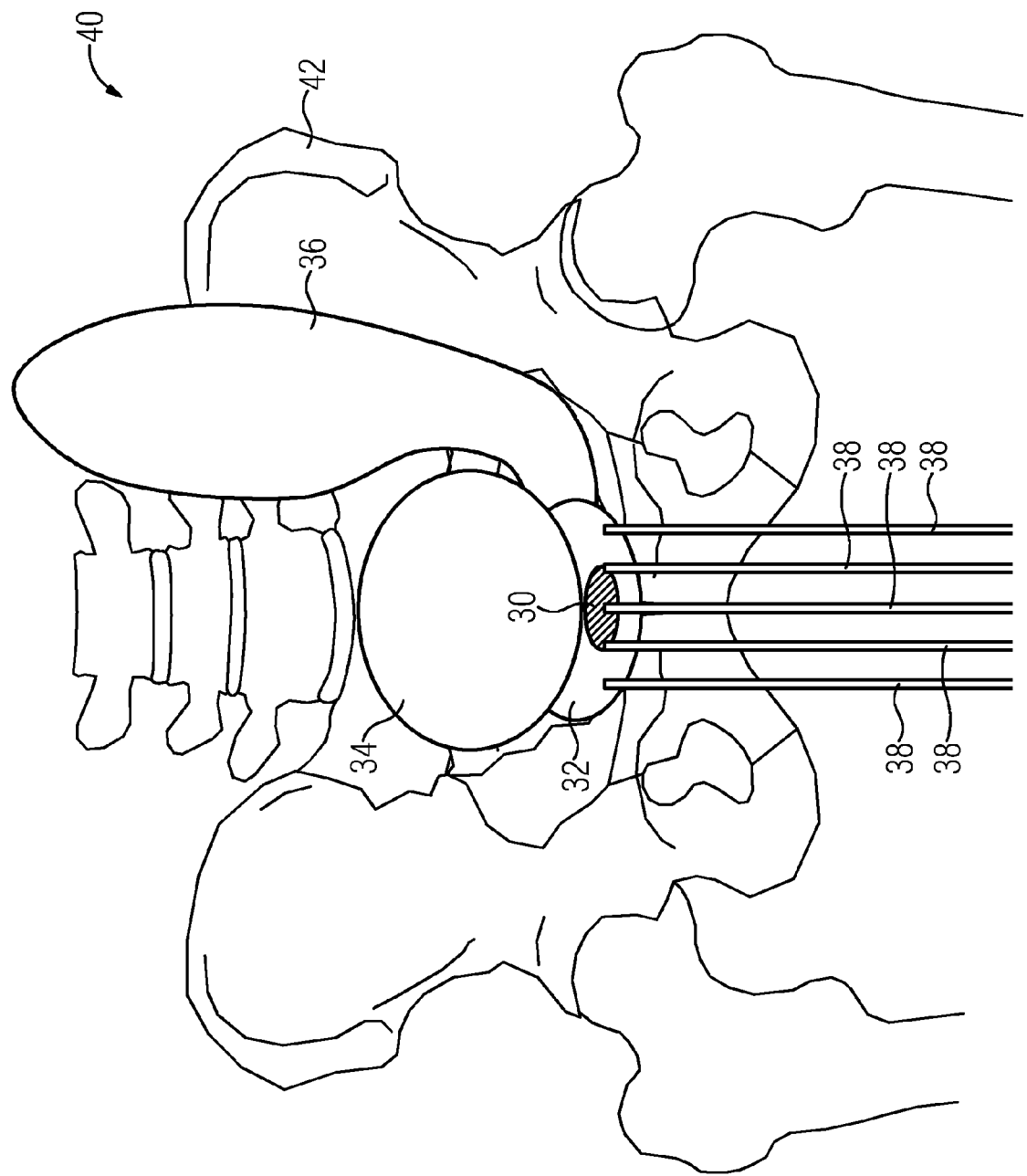
FIG. 3 shows a schematic representation of a region of the patient's body and FIG. 4 shows a schematic representation of a display of a dose distribution in a tumor generated by the navigation device from FIG. 1.

To treat the patient 10 by brachytherapy, a sequence of work steps is performed, which form a treatment protocol or workflow and by which the planning, performance and final evaluation are established for brachytherapy as an interventional method of radiotherapy. The sequence of work steps is illustrated in FIG. 2. In addition, for the explanation of the treatment protocol reference can be made to FIG. 3 and in addition it is assumed below that in the case of the patient 10 a tumor 30 in a prostate 32 is to be destroyed by brachytherapy using radioactive irradiation.

In a step S10 the patient 10 is, according to the treatment protocol, brought into a room before the actual operation, in which a preoperative 3D image dataset (PRE-OP 3D) is obtained for example by a computed tomography system and/or a magnetic resonance tomography system. A very high soft-tissue contrast is set here, so that the physician can precisely visually delimit the individual organs (e.g. the bladder 34, the rectum 36, the prostate 32 itself and where appropriate the uterus) surrounding the tumor 30. As these organs 32, 34, 36 are very sensitive to radiation, they are also included in a calculation of a radioactive radiation dose (DS) in brachytherapy in a step S12. With the help of the preoperatively obtained 3D image dataset in step S10 the physician first hereby performs the tumor diagnosis. The resulting type, position and size of the tumor 30 can hereby be determined by the physician. Based on the tumor diagnosis and the preoperatively obtained 3D image dataset the physician uses a dose planning facility, for example a personal computer with dose planning software and/or a dose planning application loaded on it, to determine a number and target positions of applicators 38 which are to be implanted into the patient 10, in order to be able to introduce radioactive material into the tumor 30. In addition the dose planning facility supplies a simulation for the dose distribution on the basis of the determined target positions of the applicator 38.

The dose planning facility can also comprise order management, which on the basis of the result of the dose planning (number of applicators 38, the strength or intensity of the individual radioactive radiation sources (seeds) which are to be introduced via the applicators 38) generates order data (ORD) in a step S14 which is suitable for use in a computer system of the hospital for ordering the radiation sources (seeds). Furthermore, other necessary materials can be ordered fully automatically in the same way. If desired, provision can also be made here for the order to be placed only where there is additional confirmation by for example the physician or other hospital personnel.

As soon as the radioactive material (where appropriate after a few days) is ready, the patient can, according to a development, be automatically booked in for the operation by the dose planning facility or else by another administration program in a step S16. The operating room can likewise be reserved and the personnel required for the operation can be scheduled fully automatically in a step S16. Use can be made here of the functionalities of a Hospital Information System (HIS) known per se. The dose planning facility must then be fitted with a corresponding software interface.

According to the operation planning the actual operation then takes place at a set time, i.e. the patient 10 is positioned on the operating table 12, the environment is sterilized, the implantation of the applicators 38 into the tumor 30 is performed and the position of the applicators 38 in the tumor 30 is checked. The steps explained below, which can be performed in connection with the operation in the sterile environment and without repositioning the patient 10, are summarized in the box OP in FIG. 2.

After successfully positioning (POS) the patient in a step S18 an intraoperatively obtained 3D image dataset (INTRA-OP 3D) is obtained in a step S20 of a region of the body 40 of the patient 10 in which the tumor 30 is located. In the present example the pelvis 42 with the organs located therein 32, 34, 36 can be mapped three-dimensionally. The 3D image dataset obtained in step S20 has a high soft-tissue contrast. Depending on the imaging unit 16 used corresponding operating parameters are provided for this from the prior art. Using the intraoperatively obtained 3D image dataset the physician obtains a precise statement about the current position of the organs 32, 34, 36 and of the tumor 30.

It can be provided that in step S20 the 3D image dataset is obtained using an especially low radiation dose if the imaging facility 16 comprises an operating mode. To this end it can then be provided that in a step S22 the intraoperative 3D image dataset obtained in this way can be merged (FUSE) with preoperatively obtained 3D image data, as was obtained for example in step S10, on the basis of anatomical landmarks. The feature of this is that the patient 10 is exposed to a lower X-ray dose because the physician needs less scans than conventional operation.

In another step S24 the control facility 24 is used to calculate a volume model (VOL) of the region of the body 40. This can be formed directly from the 3D image dataset of step S20 or from the combined 3D image dataset of step S22. The volume model can also contain a representation of the applicators 38. The applicators 38 illustrated in the volume model can here comprise the target position as was set in step S12 using the dose planning facility. The current position of the applicators 38 in the region of the body 40 can also be determined from a location facility (not shown) for instrument navigation, as is known per se from the prior art.

In order to clarify the current position of the applicators 38 in the region of the body 40 to the physician, the volume dataset of the volume model, in other words the 3D image dataset with the additional data relating to the applicators 38, as obtained in step S24, is transferred to the location facility in an embodiment of the flow trace. In a step S26 this updates the position of the applicators 38 in the volume model at predetermined time intervals and visualizes the position on the display unit 26 for the physician.

The location facility 29 here comprises markers (MARK), located by sensors, which are attached to the applicators 38, evaluation software which can be executed for example by the control facility 24 which evaluates said sensor signals, and software for generating the representation for the display facility 26. By continuously updating the position data a live image of the navigation is hereby displayed to the physician on the display unit 26. The region of the body 40 where the applicators 38 are located is displayed to the physician in the volume model. Thus without any additional fluoroscopy of the patient 10 he can position all applicators 38 precisely.

Figure 4:
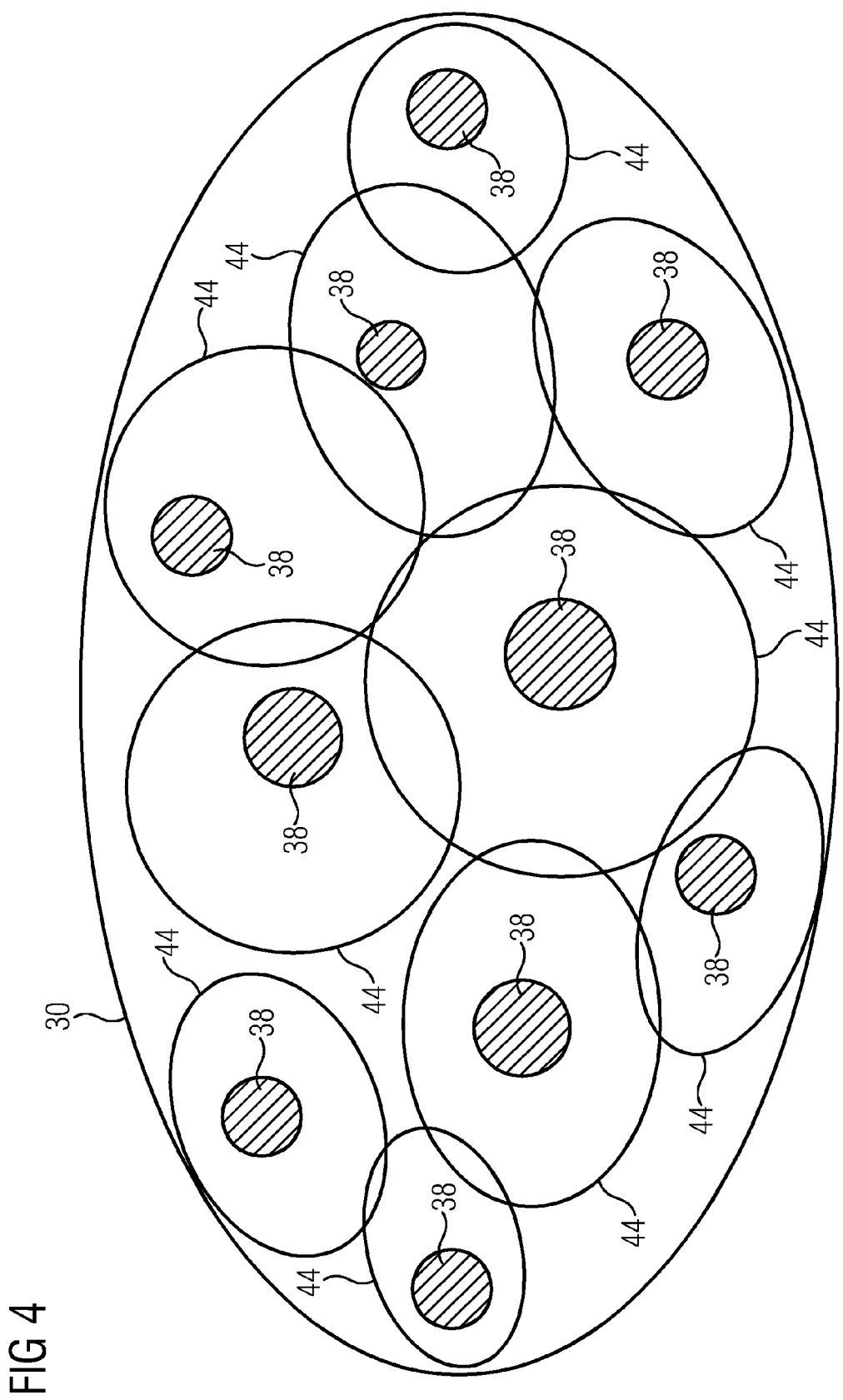

It can additionally be provided, in a step S28 on the basis of the volume model, for a dose distribution (DS DIST) of the radioactive irradiation to be determined on the basis of a simulation of the irradiation. A resultant display on the display facility 26 is represented by way of example in FIG. 4. The tumor 30 into which the applicators 38 are inserted is for example displayed to the physician in a sectional image. Depending on the position of outlet openings for radioactive radiation and the radiation intensity of the radiation sources introduced in the simulation and the dwell time of the radiation sources in the applicators 38 a radiation distribution 44 is calculated for the individual applicators and is displayed for example in the form of a closed curve. The area delimited by the respective curve of the dose distribution 44 can e.g. show that the tumor cells will be killed in the area with a predetermined probability, for example 95% and more, after the radioactive irradiation.

So far a variant of the treatment protocol has been described which uses a location facility with markers. In another variant of the treatment protocol a conventional 2D X-ray control can also be used during the operation to check the position of the applicators 38. The imaging facility 16 can also for example be used to this end, if it also enables 2D projection data to be created, in other words e.g. 2D X-ray data. This is possible for example with the X-ray flat-panel detector 22 described. An optimal C-arm position and orientation (x, y, z position, LAO, RAO, cranial/caudal) of the projection facility for monitoring the implantation of the applicators 38 can here be calculated by the control facility 24 from the 3D image dataset of step S20 or S22 obtained in the OP. It is then possible to move toward the position automatically and/or at the press of a button in a step S30. The position is optimal in the sense that the physician can identify the position of the applicators 38 on the 2D projection image dataset (2D) as far as possible e.g. free from congruence. During the implantation the physician can then execute step S30 multiple times and so monitor the position of the applicators 38.

After the implantation (POST-IMP 3D) a further 3D image dataset is obtained, still intraoperatively, with the imaging facility 16 in a step S32 and the position of the applicators 38 is checked. Step S28 can be executed again here, so that the associated dose distribution calculated by simulation is again displayed for the intraoperatively determined 3D image dataset. The physician receives a visual result of the accuracy and if necessary can make a correction directly.

For the flow trace according to FIG. 2 no final check outside the operating room is necessary, as is the case in conventional operations. The monitoring by the markers in step S28 or by the final check in step S32 already provides confirmation of the correct position of the applicators 38.

Now to conclude the operation radioactive material can be introduced into the applicators 38 in a step S34. This is provided for permanent irradiation (LD PERM). Provision can also be made to take the patient into the described afterloading room after the operation in a step S36 and to temporarily irradiate him there (LD TEMP).

In the various described variants of the flow trace an additional check on the position of the applicators 38 for example in a computed tomography system and the associated multiple repositioning of the patient become unnecessary. The intraoperative variant is used, resulting in a saving in time, resources, costs and dose. Moreover the risk of an infection or of an internal injury caused by the applicators 38 is reduced for the patient 10. Furthermore, the accuracy of the positioning of the applicators 38 is increased, because the physician is given additional opportunities to correct the position with little effort.

The example shows how the workflow in brachytherapy is optimized and completed. All necessary steps can be performed with the aid of an application if steps S12, S20, S22, S26 or S30/S32, S28 are united in one application (combination of software and hardware). It is also easy to form interfaces to an existing hospital information system, in order additionally to automate the ordering of radioactive material and the scheduling for the operation. Overall the result is an automation system which can be adjusted and/or altered individually by the physician at any time.

The intraoperative imaging (2D and 3D) enables an up-to-date statement about the precise position of the organs 32, 34, 36 is made during the operation. A check on the position of the implanted applicators 38 is likewise effected intraoperatively. No further steps apart from the operation are necessary for checking the position.

The invention claimed is:

1. A navigation device for brachytherapy, comprising
a 3D imaging facility that can be moved relative to an operating table and is adapted to obtain an intraoperative 3D image dataset for a region of a body of a patient positioned on the operating table;
an applicator that radioactively irradiates the region of the body;
a control facility that is linked to the imaging facility and is adapted to generate a volume model of the region of the body from the 3D image dataset and from position data of a spatial position of the applicator; and
a verification facility that is adapted to determine a dose distribution of the radioactive irradiation in the region of the body during the radioactive irradiation based on the volume model and a simulation of the irradiation; and
a display device that displays the dose distribution in a closed curve,
wherein the position of the applicator is emulated in the volume model, and
wherein the closed curve of the dose distribution displayed in the display device delimits an area that cells in the area will be killed with a predetermined probability after the radioactively irradiation by the applicator.

2. The navigation device as claimed in claim 1, further comprising a projection unit that can move relatively to the operating table for generating 2D projection data of the region of the body, and wherein the control facility is adapted to establish an orientation of the projection unit in respect of the operating table based on the volume model for identifying the position of the applicator on the 2D projection data.

3. The navigation device as claimed in claim 2, wherein the projection unit comprises an X-ray unit.

4. The navigation device as claimed in claim 2, further comprising a plurality of applicators, and wherein the orientation satisfies an optimization criterion so that superimposition of mappings of the applicators is minimal or at least less than a predetermined value.

5. The navigation device as claimed in claim 1, further comprising a location facility for recording a current position of the applicator and for generating corresponding current position data, and wherein the control facility is adapted to generate the volume model based on the current position data.

6. The navigation device as claimed in claim 1, further comprising a dose planning facility for determining target value data for a target position comprising the applicator in the region of the body.

7. The navigation device as claimed in claim 6, wherein the dose planning facility is adapted to determine a quantity of a radioactive material required for the irradiation and to generate order data for an order system according to a predefinable rule based on the determined quantity.

8. The navigation device as claimed in claim 1, wherein the control facility is adapted to combine the intraoperative 3D image dataset with a preoperative 3D image dataset to form a combined 3D image dataset and to generate the volume model from the combined 3D image dataset.

9. A method for performing a brachytherapy, comprising:
intraoperatively recording 3D image data by an imaging facility of a region of a body of a patient positioned on an operating table; receiving position data of an applicator by a control facility, wherein the applicator is implanted into the patient for radioactively irradiating the region of the body;
generating a volume model from the 3D image data and from the position data of the applicator and visualizing the position of the applicator on the volume model by the control facility;
determining a dose distribution of the radioactive irradiation in the region of the body during the radioactive irradiation based on the volume model and a simulation of the irradiation by a verification facility; and
displaying the dose distribution in a closed curve on a display device,
wherein the closed curve of the dose distribution displayed in the display device delimits an area that cells in the area will be killed with a predetermined probability after the radioactively irradiation by the applicator.

10. The method as claimed in claim 9, further comprising generating a 2D projection data of the region of the body by a projection unit, and wherein the control facility establishes an orientation of the projection unit in respect of the operating table based on the volume model for identifying the position of the applicator on the 2D projection data.

11. The method as claimed in claim 10, wherein the orientation satisfies an optimization criterion so that a foreshortening of a mapping of the applicator is minimal or at least less than a predefined value.

* * * * *